United States Patent
Shi et al.

(10) Patent No.: US 12,023,412 B2
(45) Date of Patent: *Jul. 2, 2024

(54) DISSOLVABLE GEL-FORMING FILM FOR DELIVERY OF ACTIVE AGENTS

(71) Applicant: SMITH & NEPHEW, INC., Memphis, TN (US)

(72) Inventors: Lei Shi, Mansfield, TX (US); Aleksa Jovanovic, Fort Worth, TX (US); Dennis Carson, Burleson, TX (US)

(73) Assignee: SMITH & NEPHEW, INC., Memphis, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/892,435

(22) Filed: Aug. 22, 2022

(65) Prior Publication Data

US 2023/0055292 A1 Feb. 23, 2023

Related U.S. Application Data

(63) Continuation of application No. 14/769,754, filed as application No. PCT/US2014/024410 on Mar. 12, 2014, now Pat. No. 11,452,698.

(Continued)

(51) Int. Cl.
*A61K 9/70* (2006.01)
*A61K 38/48* (2006.01)
(Continued)

(52) U.S. Cl.
CPC ........ *A61K 9/7007* (2013.01); *A61K 38/4873* (2013.01); *A61K 38/4886* (2013.01);
(Continued)

(58) Field of Classification Search
None
See application file for complete search history.

(56) References Cited

U.S. PATENT DOCUMENTS 3,983,209 A 9/1976 Schmitt
4,136,162 A 1/1979 Fuchs et al.
(Continued)

FOREIGN PATENT DOCUMENTS

CN 1929826 3/2007
CN 102573760 7/2012
(Continued)

OTHER PUBLICATIONS

Jen, A. et al.: "Diamonds in the Rough: Protein Crystals from a Formulation Perspective", Pharmaceutical Research, vol. 18, No. 11, (Nov. 200 l), pp. 1483-1488.

(Continued)

*Primary Examiner* — Erin M. Bowers
(74) *Attorney, Agent, or Firm* — NORTON ROSE FULBRIGHT US LLP

(57) ABSTRACT

Disclosed is a dissolvable, gel-forming film, and methods for its use, comprising a water-soluble cellulose ether, a hydrophilic rheological modifying agent, and an active proteolytic enzyme or other drug substance. The gel-forming film has a water content of less than 15% w/w and is capable of forming a hydrogel when contacted with water or other aqueous medium. The disclosed films achieve delivery of stable proteolytic enzymes to the desired site of action in a manner that provides uniform delivery of the enzymes.

21 Claims, 5 Drawing Sheets

Film product (dry)

Dissolved forming a gel

Related U.S. Application Data

(60) Provisional application No. 61/790,132, filed on Mar. 15, 2013.

(51) Int. Cl.
| | | |
|---|---|---|
| *A61K 47/10* | (2017.01) | |
| *A61K 47/38* | (2006.01) | |
| *A61L 15/28* | (2006.01) | |
| *A61L 15/38* | (2006.01) | |
| *A61L 15/44* | (2006.01) | |
| *A61L 15/60* | (2006.01) | |
| *A61L 15/62* | (2006.01) | |

(52) U.S. Cl.
CPC .............. *A61K 47/10* (2013.01); *A61K 47/38* (2013.01); *A61L 15/28* (2013.01); *A61L 15/38* (2013.01); *A61L 15/44* (2013.01); *A61L 15/60* (2013.01); *A61L 15/62* (2013.01); *C12Y 304/22002* (2013.01); *C12Y 304/24027* (2013.01)

(56) References Cited

U.S. PATENT DOCUMENTS

| | | | |
|---|---|---|---|
| 4,228,277 | A | 10/1980 | Landoll |
| 4,292,299 | A | 9/1981 | Suzuki et al. |
| 4,517,173 | A | 5/1985 | Kizawa et al. |
| 4,784,653 | A | 11/1988 | Bolton et al. |
| RE33,093 | E | 10/1989 | Schiraldi et al. |
| 5,145,681 | A | 9/1992 | Fortney et al. |
| 5,206,026 | A | 4/1993 | Sharik et al. |
| 5,393,528 | A | 2/1995 | Staab |
| 5,700,478 | A | 12/1997 | Biegajski et al. |
| 5,739,023 | A | 4/1998 | Harada et al. |
| 6,159,498 | A | 12/2000 | Tapolsky et al. |
| 6,177,096 | B1 | 1/2001 | Zerbe et al. |
| 6,228,416 | B1 | 5/2001 | Reibert et al. |
| 6,235,893 | B1 * | 5/2001 | Reibert ................... C08B 11/02 536/99 |
| 6,399,091 | B1 | 6/2002 | Berthold et al. |
| 6,458,380 | B1 | 10/2002 | Leadennan |
| 6,518,054 | B1 | 2/2003 | Van den Burg et al. |
| 6,548,556 | B2 | 4/2003 | Hobson et al. |
| 6,635,272 | B2 | 10/2003 | Leaderman |
| 6,906,043 | B2 | 6/2005 | Awamura et al. |
| 7,067,116 | B1 | 6/2006 | Bess et al. |
| 7,132,113 | B2 | 11/2006 | Zerbe et al. |
| 7,357,891 | B2 | 4/2008 | Yang et al. |
| 7,368,128 | B2 | 5/2008 | Qvist |
| 7,425,292 | B2 | 9/2008 | Yang et al. |
| 7,666,337 | B2 | 2/2010 | Yang et al. |
| 7,785,584 | B2 | 8/2010 | Jones et al. |
| 7,824,588 | B2 | 11/2010 | Yang et al. |
| 8,163,298 | B2 | 4/2012 | Griffiths-Brophy et al. |
| 9,045,743 | B2 | 6/2015 | Hoelke et al. |
| 10,058,596 | B2 | 8/2018 | Hanson |
| 2003/0008830 | A1 | 1/2003 | Prozillo |
| 2003/0027833 | A1 | 2/2003 | Cleary et al. |
| 2003/0107149 | A1 | 6/2003 | Yang et al. |
| 2003/0175333 | A1 | 9/2003 | Shefer et al. |
| 2003/0198631 | A1 | 10/2003 | Shi et al. |
| 2003/0198632 | A1 * | 10/2003 | Shi ........................ A61P 17/02 424/94.63 |
| 2004/0028739 | A1 | 2/2004 | Rippon et al. |
| 2004/0151765 | A1 | 8/2004 | Ritchie et al. |
| 2005/0118217 | A1 | 6/2005 | Barnhart et al. |
| 2005/0186257 | A1 | 8/2005 | Manegold et al. |
| 2005/0196358 | A1 | 9/2005 | Georgiades et al. |
| 2005/0208108 | A1 | 9/2005 | Jannusch et al. |
| 2006/0172000 | A1 | 8/2006 | Cullen et al. |
| 2007/0154527 | A1 | 7/2007 | Myers et al. |
| 2008/0085291 | A1 | 4/2008 | Lombardo |
| 2008/0124381 | A1 * | 5/2008 | Barnhart ............... A61K 31/716 424/443 |
| 2008/0152698 | A1 | 6/2008 | Effing et al. |
| 2008/0220029 | A1 | 9/2008 | Ng et al. |
| 2008/0254105 | A1 | 10/2008 | Tapolsky et al. |
| 2008/0279842 | A1 | 11/2008 | Qvist |
| 2009/0010910 | A1 | 1/2009 | Toren et al. |
| 2010/0021416 | A1 | 1/2010 | Lichter et al. |
| 2010/0159564 | A1 | 6/2010 | Dwulet et al. |
| 2011/0190722 | A1 | 8/2011 | Munro et al. |
| 2013/0045196 | A1 | 2/2013 | Shi et al. |
| 2014/0154235 | A1 | 6/2014 | Shi et al. |
| 2015/0283217 | A1 | 10/2015 | Shi et al. |

FOREIGN PATENT DOCUMENTS

| | | |
|---|---|---|
| GB | 2147206 | 5/1985 |
| JP | 2006-503044 | 1/2006 |
| JP | 2007-500673 | 1/2007 |
| JP | 2007/52673 | 9/2007 |
| JP | 2011/507920 | 3/2011 |
| RU | 2276998 | 5/2006 |
| WO | WO 1999/044631 | 9/1999 |
| WO | WO 2004/009050 | 1/2004 |
| WO | WO 2005/035010 | 4/2005 |
| WO | WO 2006/037606 | 4/2006 |
| WO | WO 2007/128985 | 11/2007 |
| WO | WO 2010/038231 | 4/2010 |
| WO | WO 2011/071986 | 6/2011 |
| WO | WO 2012/155027 | 11/2012 |
| WO | WO 2013/170128 | 11/2013 |

OTHER PUBLICATIONS

Lin et al., Hydrogels in controlled release formulations: Network design and mathematical modeling, Advanced Drug Delivery Reviews 58 (2006) 1379-1408.

Notice for Reasons of Rejection issued in Japanese Application No. 2016501524, dated Oct. 4, 2017 (English translation provided).

Search Report issued in Russian Patent Application No. 2015137174, dated Jan. 25, 2018.

Shenoy, B. et al.: "Stability of Crystalline Proteins", Biotechnology and Bioengineering, vol. 73, No. 5, (Jun. 2001), pp. 358-369.

Ashland Physical Chemical Property Book, "Klucel™ hydroxypropylcellulose Physical and Chemical Properties," 2017.

Ashland Product Data "Natrosol™ 250 Water Soluble Hydroxyethylcellulose, "Ashland Specialty Ingredients, 2015.

Milne, C.T., et al., "A comparison of collagenase to hydrogel dressings in wound debridement", Wounds 2010, vol. 22, No. 11, Retrieved from https://www.woundsresearch.com/content/comparison-collagenase-hydrogel-dressings-wound-debridement. Accessed Jun. 12, 2020, 5 pages.

Office Action issued in corresponding Canadian Application No. 2,890,757, dated May 11, 2020.

Office Action issued in Japanese Application No. 2015-542048, issued Sep. 11, 2017 (with English translation).

\* cited by examiner

Film product (dry)

Dissolved forming a gel

-will stay in the wound bed
(current and past animal study film formulation)

-will "leak" off of the wound bed

1. Moisten wound with saline

2. Apply film to moistened wound

3. Film after application on wound.

4. Moisten film with saline after applying to the wound

5. Apply a nonstick dressing, presoaked in saline, on top of the film

6. Secure the dressings with Tegaderm and tape

DISSOLVABLE GEL-FORMING FILM FOR DELIVERY OF ACTIVE AGENTS

CROSS REFERENCE TO RELATED APPLICATIONS

This application is a continuation of U.S. patent application Ser. No. 14/769,754, filed Aug. 21, 2015, which is a national phase application under 35 U.S.C. § 371 of International Pat. App. No. PCT/US2014/024410 filed Mar. 12, 2014, which claims the benefit of U.S. Prov. App. No. 61/790,132 filed Mar. 15, 2013. The contents of each application are incorporated into the present specification by reference.

BACKGROUND OF THE INVENTION

A. Field of the Invention

The invention generally relates to methods and compositions useful for treating wounds with a dissolvable, gel-forming film that releases enzyme actives onto the wound site upon dissolving.

B. Description of Related Art

The presence of eschar and other necrotic tissue in a wound can impede the healing process, causing the wound to become a slow-healing or "chronic" wound. Diabetic foot ulcers, venous leg ulcers, arterial leg ulcers, decubitus ulcers, stasis ulcers, dermal ulcers, burns, and pressure ulcers are examples of such wounds.

Enzymatic wound debridement agents can be used to digest eschar and other necrotic tissue, thereby facilitating the healing process of wounds. Such agents are enzymes that can digest eschar and other necrotic tissue. Proteolytic enzymes are preferred, as eschar wounds often contain a wide diversity of proteins. However, it is difficult to maintain stability of such enzymes in a commercial product. Because proteolytic enzymes are capable of autolysis, it is difficult to deliver them to the wound site in a manner that maintains the activity and stability of the enzyme. Moreover, current means for providing debriding agents to a wound site do not uniformly deliver the debriding agent to the entire affected area.

Thus, there remains a need for a solution that effectively balances enzyme activity with enzyme stability, and also provides for uniform deliver of the enzyme across the area to be treated.

SUMMARY OF THE INVENTION

The inventors provide a dissolvable, gel-forming film for delivering active agents, such as those used to treat wounds. The film is solid and non-flowable, but has the ability to dissolve upon contact with water or other aqueous medium (e.g., buffer or saline solution or from the wound itself) to form a hydrogel that remains on the wound, as described herein. This film solves the problems of (1) balancing enzyme activity and stability in a formulation that provides optimal conditions for enzyme function and (2) non-uniform delivery of the semisolid product, resulting in poor dose control. By way of example, a dissolvable, gel-forming film comprising a water-soluble ether, a hydrophilic rheological modifying agent, and a proteolytic enzyme (e.g., thermolysin) is provided. Such a composition is easily applied to a wound as a dry film, which is then dissolved with water or other aqueous medium to form a hydrogel and release the enzymes and/or other drug substances in active form and uniformly to the wounded area.

In some aspects, there is disclosed a dissolvable, gel-forming film comprising: a water-soluble cellulose ether; a hydrophilic rheological modifying agent; and a proteolytic enzyme, wherein the dissolvable, gel-forming film has a water content of less than 15% w/w, and the dissolvable, gel-forming film is capable of forming a hydrogel when contacted with water or other aqueous medium. Non-limiting examples of cellulose ethers are provided throughout this specification. Such examples include a hydroxyalkyl cellulose ether (e.g., hydroxyethylcellulose, hydroxypropylcellulose, or hydroxypropylmethylcellulose, or any combination thereof or all of said cellulose ethers). In some aspects, the cellulose ether can be a non-ionic cellulose ether. The amount of the water-soluble cellulose ether or hydrophilic rheological modifying agent within the film can vary as needed to achieve a particular viscosity in the hydrogel that is formed when the film is hydrated. The film is considered "dry" or "dehydrated" when it has a water content of less than 15% w/w. The film may, for example, have a water content of 0, 1, 2. 3, 4, 5, 6, 7, 8, 9, 10, 11, 12, 13, or 14% w/w, or any percentage derivable therein. In certain embodiments, the hydrogel resulting from the film being dissolved in water or other aqueous medium has a viscosity of between 1,000 to 100,000 cps, as measured using a Brookfield RV Model Viscometer using small sample adapter with spindle #SC4-14 and chamber #SC4-6R, at 10 rpm at room temperature, reading taken at 1 minute. For example, the hydrogel resulting from the film being dissolved in water or other aqueous medium may have a viscosity of 1,000, 5,000, 10,000, 15,000, 20,000, 25,000, 30,000, 35,000, 40,000, 45,000, 50,000, 55,000, 60,000, 65,000, 70,000, 75,000, 80,000, 85,000, 90,000, 95,000, or 100,000 cps, or any viscosity derivable therein, as measured using a Brookfield RV Model Viscometer using small sample adapter with spindle #SC4-14 and chamber #SC4-6R, at 10 rpm at room temperature, reading taken at 1 minute.

The dissolvable, gel-forming film may contain any proteolytic enzyme that would be selected by one or ordinary skill in the art for a desired effect. Certain, non-limiting examples of proteolytic enzymes include themolysin, collagenase, and papain. In particular embodiments, the proteolytic enzyme is thermolysin. In certain embodiments, the proteolytic enzyme is in crystalline form.

The thickness of the film can be adjusted based on the desired use. For example, the thickness of the film can range from 10 to 1000 µm. In particular embodiments, the thickness of the film is 10, 20, 30, 40, 50, 60, 70, 80, 90, 100, 150, 200, 250, 300, 350, 400, 450, 500, 550, 600, 650, 700, 750, 800, 850, 900, 950, or 100 µm, or any thickness derivable therein.

The dissolvable, gel-forming films are capable of forming a hydrogel when contacted with water or other aqueous medium. For example, the film may be capable of dissolving in water or other aqueous medium at a rate from 0.1 to 100 mg/min. In some embodiments, the film is capable of dissolving in water or other aqueous medium at a rate of 0.1, 0.2, 0.3, 0.4, 0.5, 0.6, 0.7, 0.8. 0.9. 1, 5, 10, 15, 20, 25, 30, 35, 40, 45, 50, 55, 60, 65, 70, 75, 80, 85, 90, 95, or 100 mg/min, or any rate derivable therein. In certain embodiments, the dissolvable, gel-forming film is capable of dissolving in water or other aqueous medium at a rate from 0.5-10 mg/min. For example, the film may be capable of dissolving in water or other aqueous medium at a rate of 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, or 10.0 mg/min, or any rate derivable therein.

The dissolvable, gel-forming film may contain any weight percent of the proteolytic enzyme that one of ordinary skill in the art would choose to achieve a desired result. In some embodiments, the weight percent is not less than 0.1% of the dry weight of the film and does not decrease by more than 10% when stored at room temperature (defined as 20° C. to 25° C.) for 24 months. In some embodiments, the film may contain a proteolytic enzyme in crystalline form.

The dissolvable, gel-forming film may comprise any percentage of the water-soluble cellulose ether or combinations thereof as chosen by one of ordinary skill in the art to achieve a desired result. In some aspects, the film comprises 50 to 70% w/w or 55 to 65% w/w of the water-soluble cellulose ether or combinations thereof. For example, the film may comprise 50, 51, 52, 53, 54, 55, 56, 57, 58, 59, 60, 61, 62, 63, 64, 65, 66, 67, 68, 69, or 70%, or any percentage derivable therein, w/w of the water-soluble cellulose ether or combinations water-soluble cellulose ethers. For example, in some embodiments, the film comprises 25 to 35% w/w of hydroxyethylcellulose and 25 to 35% w/w of hydroxypropylmethyl cellulose.

The dissolvable, gel-forming film may comprise any percentage of a hydrophilic rheological modifying agent as chosen by one of ordinary skill in the art to achieve a desired result. In some aspects, the film comprises 15 to 25% w/w of the hydrophilic rheological modifying agent. Non-limiting examples of hydrophilic rheological modifying agents include a polyol (e.g., polyethylene glycol (PEG)), Glycerin, and Propylene Glycol. In certain embodiments, the polyol is polyethylene glycol (PEG). In some embodiments, the polyethylene glycol is PEG-400 or PEG-600.

The dissolvable, gel-forming film may comprise any percentage of proteolytic enzyme. For example, the film may comprise 5 to 15% w/w of the proteolytic enzyme. In some aspects, the film comprises 5, 6, 7, 8, 9, 10, 11, 12, 13, 14, or 15%, or any percentage derivable therein, w/w of the proteolytic enzyme. In some embodiments, the film may comprise a proteolytic enzyme in crystalline form.

In some embodiments, the dissolvable, gel-forming film includes a metal salt. For example the metal salt may be sodium chloride or calcium chloride or mixtures thereof. The film may also include a preservative, such as, for example, methylparaben, propylparaben, or phenoxyethanol, or mixtures thereof. In certain embodiments, the film is sterile.

In certain aspects, the dissolvable, gel-forming film is produced by: (a) obtaining a first mixture comprising 3 to 7% w/w of the cellulose ether or combinations thereof, 1 to 3% w/w of the hydrophilic rheological modifying agent, and Tris Buffer (10 mM, pH=7.5); (b) obtaining a second mixture comprising a proteolytic enzyme, a metal salt, and Tris Buffer (10 mM, pH=7.5); (c) mixing the first and second mixtures together to obtain a hydrogel; and (d) drying the hydrogel from step (c) to obtain the dissolvable, gel-forming film. Such a film produced in this manner may contain any of the proteolytic enzymes described herein (e.g., themolysin, collagenase, or papain). In certain aspects such a film includes thermolysin.

Also disclosed are methods of treating or debriding a wound comprising topically applying any of the dissolvable, gel-forming films disclosed herein to a wound in need of debridement. Such a wound may be a chronic wound. Non-limiting examples of chronic wounds that may benefit from the disclosed compositions and methods include a diabetic foot ulcer, a venous leg ulcer, an arterial leg ulcer, a decubitus ulcer, a stasis ulcer, a dermal ulcer, a burn, or a pressure ulcer. A wound that is debrided may include necrotic tissue, such as, for example, an eschar.

In the disclosed methods, water or other aqueous medium may be applied to the wound before the dissolvable, gel-forming film is applied to the wound. In some aspects, water or other aqueous medium is applied to the dissolvable, gel-forming film after the film is applied to the wound. In some embodiments, water or other aqueous medium may be applied to the wound before application of the dissolvable, gel-forming, film, and water or other aqueous medium may also be applied to the dissolvable, gel-forming film after the film is applied to the wound. In each of these cases, water or other aqueous medium will contact the film and cause the hydrogel to form. One example of an aqueous medium that may be useful is a saline solution. In addition, in some aspects, a bandage, wound dressing, or gauze may be applied onto the dissolvable, gel-forming film after the film is applied to the wound.

The term "room temperature" is defined as 20° C. to 25° C.

The term "about" or "approximately" are defined as being close to as understood by one of ordinary skill in the art, and in one non-limiting embodiment the terms are defined to be within 10%, preferably within 5%, more preferably within 1%, and most preferably within 0.5%.

The terms "inhibiting," "reducing," "treating," or any variation of these terms, includes any measurable decrease or complete inhibition to achieve a desired result. For example, in certain embodiments, "treating" refers to a reduction in eschar on a wound. Similarly, the term "effective" means adequate to accomplish a desired, expected, or intended result.

The use of the word "a" or "an" when used in conjunction with the term "comprising" may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The compositions and methods for their use can "comprise," "consist essentially of," or "consist of" any of the ingredients or steps disclosed throughout the specification. With respect to the transitional phase "consisting essentially of," in one non-limiting aspect, a basic and novel characteristic of the compositions and methods disclosed in this specification includes the film's ability to stabilize a proteolytic enzyme and provide for uniform delivery of the active proteolytic enzymes to a wound site.

It is contemplated that any embodiment discussed in this specification can be implemented with respect to any method or composition of the invention, and vice versa. Furthermore, compositions of the invention can be used to achieve methods of the invention.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF ILLUSTRATIVE EMBODIMENTS

Figure 1:
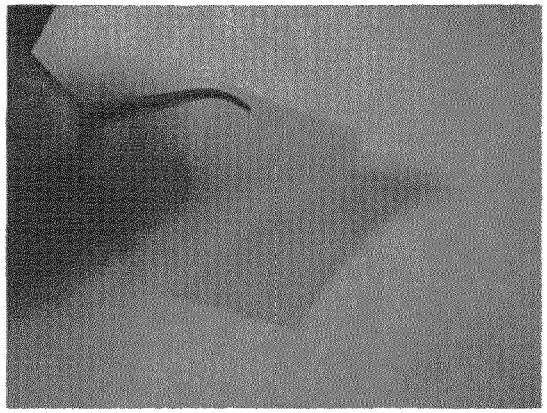
FIG. 1. An illustration showing the application of the dry film product, which then dissolves to form a gel.
Figure 1:
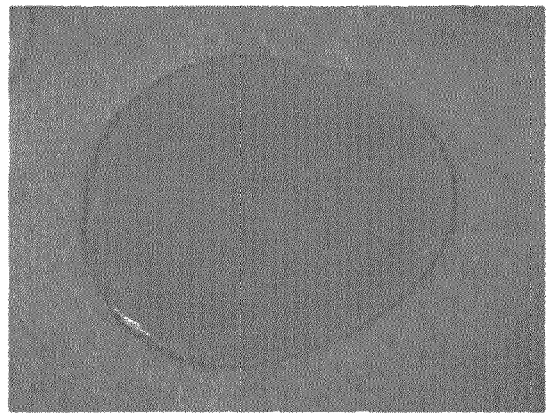

Effective wound cleansing and debridement help facilitate the healing process. Devitalized tissue present in a wound bed is undesirable—it serves as a reservoir for bacterial growth, contains elevated levels of inflammatory mediators that promote chronic inflammation at the wound site, and impairs cellular migration. The four most common methods used to debride a wound include surgical, autolytic, enzymatic, and mechanical debridement.

With respect to enzymatic debridement, currently SANTYL® Collagenase Ointment is the only approved debriding drug product in the U.S. marketplace. This product is a hydrophobic ointment that utilizes collagenase as the debriding agent. While others have attempted to use different debriding agents and various formulations, problems faced include lack of stability and lack of uniform delivery. These problems associated with debriding agents limit their use to effectively debride wounds.

The inventors provide a dissolvable, gel-forming film for delivering active agents, such as those used to treat wounds. This film solves the problems of (1) balancing enzyme activity and stability in a formulation that provides optimal conditions for enzyme function and (2) non-uniform delivery of the semisolid product, resulting in poor dose control. By way of example, a dissolvable, gel-forming film comprising a water-soluble ether, a hydrophilic rheological modifying agent, and a proteolytic enzyme (e.g., thermolysin) is provided. Such a composition is easily applied to a wound as a dry film, which is then dissolved to form a hydrogel and to release the enzymes and/or other drug substances in active form and uniformly to the wounded area.

A. Films

The compositions of the present invention are formulated as films. In particular, dehydrated films are provided that contain enzyme actives in a crystal state. Upon dissolving, a hydrogel is formed, and the enzymes become active and are released from the formed hydrogel.

1. Proteolytic Enzymes

Proteolytic enzymes may be useful in the disclosed methods and compositions, particularly in applications directed to wound treatment. Useful proteolytic enzymes include thermolysin, collagenase, papain, and other proteases.

Thermolysin is a thermostable metalloproteinase that cleaves at the N-terminus of the hydrophobic residues leucine, phenylalanine, valine, isoleucine, alanine and methionine. The optimal digestion temperature range is 30-85° C. Thermolysin activity is optimal at pH 5.0-8.5. There are several commercial sources for this enzyme. One such source is lyophilized thermolysin sold by Promega Corporation (Madison, Wisconsin (USA)). Another lyophilized thermolysin product is sold by Sigma-Aldrich (St. Louis, Missouri (USA)). The thermolysin from both products was obtained from *Bacillus thermoproteolyticus* rokko. A further manufacturer and supplier of thermolysin is Amano Enzyme, Inc., Japan. The CAS No. for thermolysin is 9073-78-3.

Collagenase is a metalloproteinase derived from the bacteria *Clostridium histolyticum*. It is particularly useful for digesting collagens. There are two collagenase genes found in *C. histolyticum*, col G and col H. Both can work together to break down collagen substrates. The optimal pH for the collagenase is between 6-9, and it is generally stable as compared to other proteases. The current collagenase product on the U.S. market is produced by Healthpoint Biopharmaceuticals.

Papain is another widely used protease that is obtained from the *Papaya* tree. Unlike thermolysin and collagenase, papain is a cysteine protease. It is a non-specific protease that is able to digest a large variety of proteins. It is less stable as compared to thermolysin or collagenase, and autolytic degradation of papain is expected to be significant. Papain can function in a wide range of pH conditions, with an optimal pH of 6. Although papain was historically used for wound debridement, there are no approved, commercially-available papain products in the U.S.

2. Cellulose Ethers

Cellulose ethers are high-molecular-weight compounds that can be made by replacing the hydrogen atoms of hydroxyl groups in the glucose units of cellulose with alkyl, hydroxylalkyl, or carboxyalkyl groups. Non-limiting examples of alkyl cellulose ethers include methyl cellulose (MC), ethyl cellulose (EC), and ethyl methyl cellulose (EMC). Non-limiting examples of hydroxyalkyl cellulose ethers include hydroxyethyl cellulose (HEC), hydroxylpropyl cellulose (HPC), hydroxymethyl cellulose (HMC), hydroxypropylmethyl cellulose (HPMC), ethylhydroxyethyl cellulose (EHEC), hydroxyethylmethy cellulose (HEMC), methylhydroxyethyl cellulose (MHEC), methylhydroxypropylcellulose (MHPC), and hydroxyethylcarboxymethyl cellulose (HECMC). Non-limiting examples of a carboxyalkyl cellulose ethers include carboxymethyl cellulose (CMC) and carboxymethylhydroxyethylcellulose (CMHEC). In some particular aspects, the cellulose ether can be a non-ionic cellulose ether. As with thermolysin, there are a wide range of commercial sources for each of these cellulose ethers (e.g., Dow Chemical Company (USA), Ashland (USA), Samsung Fine Chemicals (USA)). Additional commercial sources of these cellulose ethers can be found in the International Cosmetic Ingredient Dictionary and Handbook, $12^{th}$ Edition (2008), volumes 1-3.

3. Hydrophilic Rheological Modifying Agents

Hydrophilic rheological modifying agents have an affinity for water and affect the flow properties of a composition containing them. One example of a hydrophilic rheological modifying agent is polyethylene glycol (PEG). Other examples include Glycerin and Propylene Glycol, Di-Propylene Glycol, Butylene Glycol and other glycol-based excipients. Some hydrophilic rheological modifying agents also serve as plasticizers to enhance desired properties for the films. The amount of such rheological modifying agents can range from 15 to 25% w/w, although more or less can be added to achieve a desired result (for example, varying the viscosity of the hydrogel that results when the film is dissolved).

Polyethylene glycols (PEGs) are homo-polymers of ethylene glycol and water represented by the formula: $H(OCH_2CH_2)_nOH$ in which n represents the average number of oxyethylene groups. Polyethylene glycols can be either liquid or solid at 25° C. depending on their molecular weights.

The following non-limiting examples are suitable for use with the disclosed compositions and methods and are described using U.S. Pharmacopeial Convention (USP) nomenclature: polyethylene glycol 200, polyethylene glycol 300, polyethylene glycol 400, polyethylene glycol 500, and polyethylene glycol 600.

The following non-limiting examples of solid polyethylene glycols are suitable for use with the disclosed compositions and methods and are described using USP nomenclature: polyethylene glycol 700, polyethylene glycol 800, polyethylene glycol 900, polyethylene glycol 1000, polyethylene glycol 1100, polyethylene glycol 1200, polyethylene glycol 1300, polyethylene glycol 1400, polyethylene glycol 1450, polyethylene glycol 1500, polyethylene glycol 1600, polyethylene glycol 1700, polyethylene glycol 1800, polyethylene glycol 1900, polyethylene glycol 2000, polyethylene glycol 2100, polyethylene glycol 2200, polyethylene glycol 2300, polyethylene glycol 2400, polyethylene glycol 2500, polyethylene glycol 2600, polyethylene glycol 2700, polyethylene glycol 2800, polyethylene glycol 2900, polyethylene glycol 3000, polyethylene glycol 3250, polyethylene glycol 3350, polyethylene glycol 3750, polyethylene glycol 4000, polyethylene glycol 4250, polyethylene glycol 4500, polyethylene glycol 4750, polyethylene glycol 5000, polyethylene glycol 5500, polyethylene glycol 6000, polyethylene glycol 6500, polyethylene glycol 7000, polyethylene glycol 7500, and polyethylene glycol 8000.

Such liquid and solid polyethylene glycols are available commercially from the DOW Chemical Company under the CARBOWAX™ trade name and from the BASF Corporation under LUTROL® E and PLURACARE® E trade names. Both pharmaceutical grade (USP/NF) and cosmetic grade polyethylene glycols are suitable for use in the disclosed compositions and methods.

4. Additives

In addition to the enzymes, cellulose ethers, and rheological modifying agents listed above, the films can include additional ingredients. For instance, salts such as $NaCl_2$ or $CaCl_2$ can be used as stabilization agents. The amounts of salt can range from 0.01 to 1% w/w, although more or less can be added to achieve a desired result. Plasticizers may also be added. Preservatives such as methyl and propyl parabens, phenoxy ethanol, and others known to those of skill in the art can be used. The amounts of such preservatives can range from 0.01 to 1% w/w, although more or less can be added to achieve a desired result. Buffers having an appropriate pH range (e.g., 5 to 9) for the desired enzymatic activity can be used. An example of such a buffer is Tris buffer (10 mM, pH=7.5). The source of water or other aqueous medium for dissolving the film can come from a buffer solution or saline solution. Further additives can be added to achieve a given tactile property or to add an additional functional aspect to the film or resulting hydrogel (e.g., agents that can further aid in the wound healing process such as antimicrobial agents, anti-inflammatory agents, pain-relieving agents, etc.).

5. Preparation of the Dissolvable, Gel-Forming Films

The films of the present invention can be prepared by any methods known to those of ordinary skill in the art. In particular embodiments, one or more buffer solutions or other aqueous mediums of cellulose ethers are mixed. Upon homogenization, various plasticizers and rheology modifying agents can be added, such as PEG, Glycerin and Propylene Glycol. Next, the enzyme may be added as a solution or dispersion in buffer with appropriate amounts of salts, such as NaCl and $CaCl_2$. The final mixture may be stirred until homogeneous. The mixture (a viscous gel) can then be centrifuged to remove air bubbles, and an appropriate quantity may be casted into petri dishes. The dishes may be left to dry on even surfaces with appropriate ventilation under normal lab conditions. After about 48 h of drying, the films may be cut into custom size pieces for use.

In some embodiments, the composition before drying comprises the following ingredients: (a) 3 w % of Hydroxy-Ethyl Cellulose (HEC, Natrosol 250 HX Pharm-Aqualon) in Tris Buffer (10 mM, pH=7.5); (b) 2.5 w % of Hydroxypropyl MethylCellulose (HPMC, Methocel K-15M, DOW Chemical) in Tris Buffer (10 mM, pH=7.5); (c) Polyethylene Glycol PEG-600 (Carbowax Sentry, DOW Chemical) and (d) Enzyme, along with NaCl and $CaCl_2$ in Tris Buffer (10 mM, pH=7.5).

For example, in one embodiment, 79 g of 3 w % HEC, 87 g of 2.5 w % HPMC, 1.6 of Polyethylene Glycol 600 (PEG-400) are mixed with a mechanical stirrer until homogeneous. The active phase consists of 0.87 g of enzyme (thermolysin), 0.22 g of NaCl and 0.11 g of $CaCl_2$ in 31.5 g of Tris Buffer (10 mM, pH=7.5). Upon homogenization, the active phase was added to the mixture and stirred for not less than 2 hours. The mixture was then degassed for 15-20 min to remove the air bubbles. The mixture was then transferred into a petri dish (φ15 cm, about 45 gms of the mixture per dish) and placed in a gel drier overnight. The concentration of components in the dry film were as follows: HEC 30-32 w %; HPMC 29-30 w %; PEG-400 21-22 w %; Enzyme 9-11% NaCl 2.5-3.5 w %; and $CaCl_2$ 1-2 w %.

The viscosities of the hydrogels formed after hydration of the films are generally in the range of 5,000-100,000 when approximately 1 g of dry film is solubilized in 20 ml of aqueous medium. For example, the hydrogel resulting from film "A01" used in the experiments described in FIGS. 3 and 4 has a viscosity of 59,400 cps. The hydrogel resulting from a film similar to the faster dissolvable film used in the experiment described in in FIG. 6 has a viscosity of 22,600 cps under similar conditions. Viscosity was measured using a Brookfield RV Model Viscometer using small sample adapter with spindle #SC4-14 and chamber #SC4-6R, at 10 rpm at room temperature, reading taken at 1 minute.

B. Methods of Using the Dissolvable, Gel-Forming Films

The dissolvable, gel-forming films of the present invention may be used in a variety of methods. For instance, they can be used to debride wounds such as chronic wound. Such methods include applying to the wound a composition comprising thermolysin (e.g., via topical application). After application, the wound may be covered with a wound dressing such as a gauze pad. The film may be applied to a dressing such as a gauze pad first and then applied to the wound surface. The application amount depends on the severity and type of the wound and nature of the subject.

In certain aspects, the film can be applied to the wound periodically, for example, daily, twice daily, once every other day, once a week, as needed. A therapeutic regimen can be used that includes periodic dressing changes with wound cleansing and application of fresh composition between changes until the debridement of the necrotic tissue is complete.

A wide variety of wounds can be treated with the films of the present invention. Examples include burns, acute wounds, or chronic wounds. Non-limiting examples of chronic wounds include diabetic foot ulcers, venous leg ulcers, arterial leg ulcers, decubitus ulcers, stasis ulcers, dermal ulcers, burns, and pressure ulcers.

C. Kits

Kits are also contemplated as being used in certain aspects of the invention. For instance, a film of the present invention can be included in a kit. A kit can include a container. Containers can include a case, sachet, pouch, dispenser, package, compartment or other containers into which the films are retained. The kit can include indicia on its surface. The indicia, for example, can be a word, a phrase, an abbreviation, a picture, or a symbol The containers can store or dispense a pre-determined size of the film or a roll of the film. The containers can contain one individually wrapped film or several layers of the film. A kit can also include instructions for using the kit and/or compositions.

Further, the films of the present invention may also be sterile, and the kits containing such films can be used to preserve the sterility. The films may be sterilized via an aseptic manufacturing process or sterilized after packaging by methods known in the art.

D. Examples

The following examples are included to demonstrate certain non-limiting aspects of the invention. It should be appreciated by those of skill in the art that the techniques disclosed in the examples that follow represent techniques discovered by the applicants to function well in the practice of the invention. However, those of skill in the art should, in light of the present disclosure, appreciate that many changes can be made in the specific embodiments that are disclosed and still obtain a like or similar result without departing from the spirit and scope of the invention.

1. Dissolvable, Gel-Forming Films

Dissolvable, gel-forming films were prepared generally as follows. Proteolytic enzymes were formulated in a hydrophilic gel and then cast into a shaped mold and allowed to dry. A dry film was formed in a pre-designed size and shape. The moisture content was controlled to a very low level, for instance, approximately 5%. This dry state increases the stability of the enzyme, especially when the enzyme is in crystalline form. Prior to wound application, the film can be cut into the appropriate size and shape. Prior to application, the film may be moistened with water or other aqueous medium, followed by placing it on the wound surface and covering it with a moistened gauze or dressing (see FIGS. 1 and 5). The film then slowly dissolves and becomes a hydrogel that can readily release the enzyme to the wound (see FIG. 1). Such films effectively debride wounds in an animal model, as discussed below. Stability testing demonstrated that even at 40° C., the dry film can maintain stable enzymatic activity for unexpectedly extended periods of time during storage The viscosities of hydrogels that result when the films are hydrated are generally in the range of 5,000-100,000 when approximately 1 g of dry film is solubilized in 20 ml of aqueous medium. For example, hydrogels resulting from hydration of film "A01" (as used in the experiments described in FIGS. 3 and 4) have a viscosity of 59,400 cps. The viscosity measurements were taken using a using a Brookfield RV Model Viscometer using small sample adapter with spindle #SC4-14 and chamber #SC4-6R, at 10 rpm at room temperature, reading taken at 1 minute. The following Table 1 provides dissolving and viscosity characteristics of films having different compositions upon exposure of the films to normal saline solution.

TABLE 1

Dissolving characteristics of gel-forming films upon exposure to normal saline

| Lot | Description | HEC (wt %) | HPMC HMW (wt %) | HPMC LMW (wt %) | HPC SL (wt %) | PEG-600 (wt %) | Sorbitol (wt %) | Gel Formation (h) | Viscosity (cps) |
| --- | --- | --- | --- | --- | --- | --- | --- | --- | --- |
| 038-1118A01 (45 g) | Several animal studies (A11-002), (A10-009), A01 in AWE experiments | 35 | 32 | 0 | 0 | 23 | 0 | >1 h | 59400 |
| 038-0405802 (60 g) | Animal study (A11-004) | 20 | 0 | 0 | 51 | 21 | 0 | <1 h | 13000 |
| 038-0405803 (60 g) | Prototype | 21 | 0 | 43 | 0 | 23 | 0 | <1 h | 6000 |
| 038-0405803 | Prototype | 21 | 0 | 43 | 0 | 23 | 0 | <1 h | 5700 |

TABLE 1-continued

Dissolving characteristics of gel-forming films upon exposure to normal saline

Figure 3:
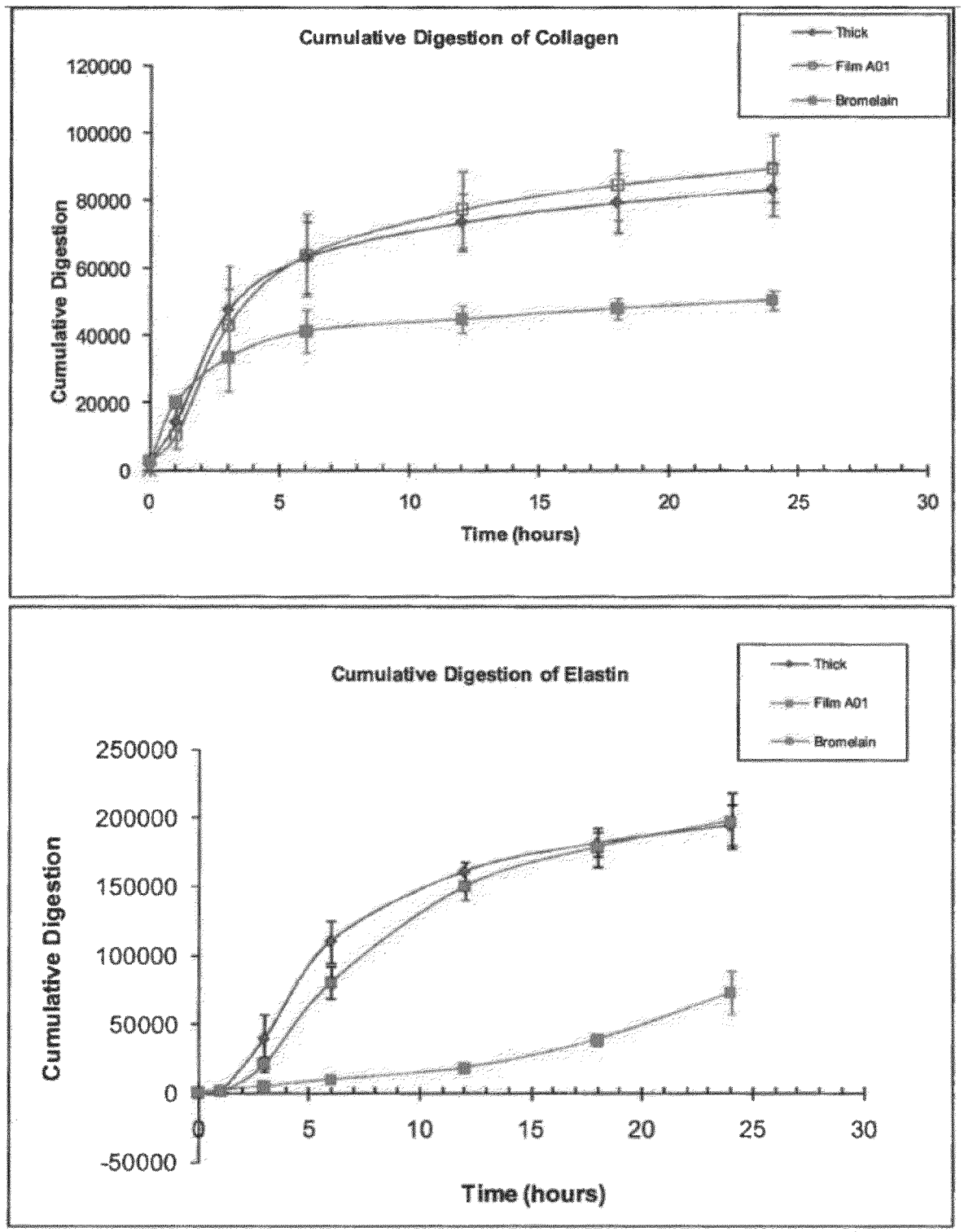
FIG. 3. A debridement experiment conducted in vitro using artificial eschar prepared using collagen or elastin. Film containing thermolysin was compared with a thermolysin gel and a Bromelain gel. Both the film and the thermolysin gel digested collagen and elastin more effectively than the Bromelain gel, which contained 10% bromelain.
Figure 4:
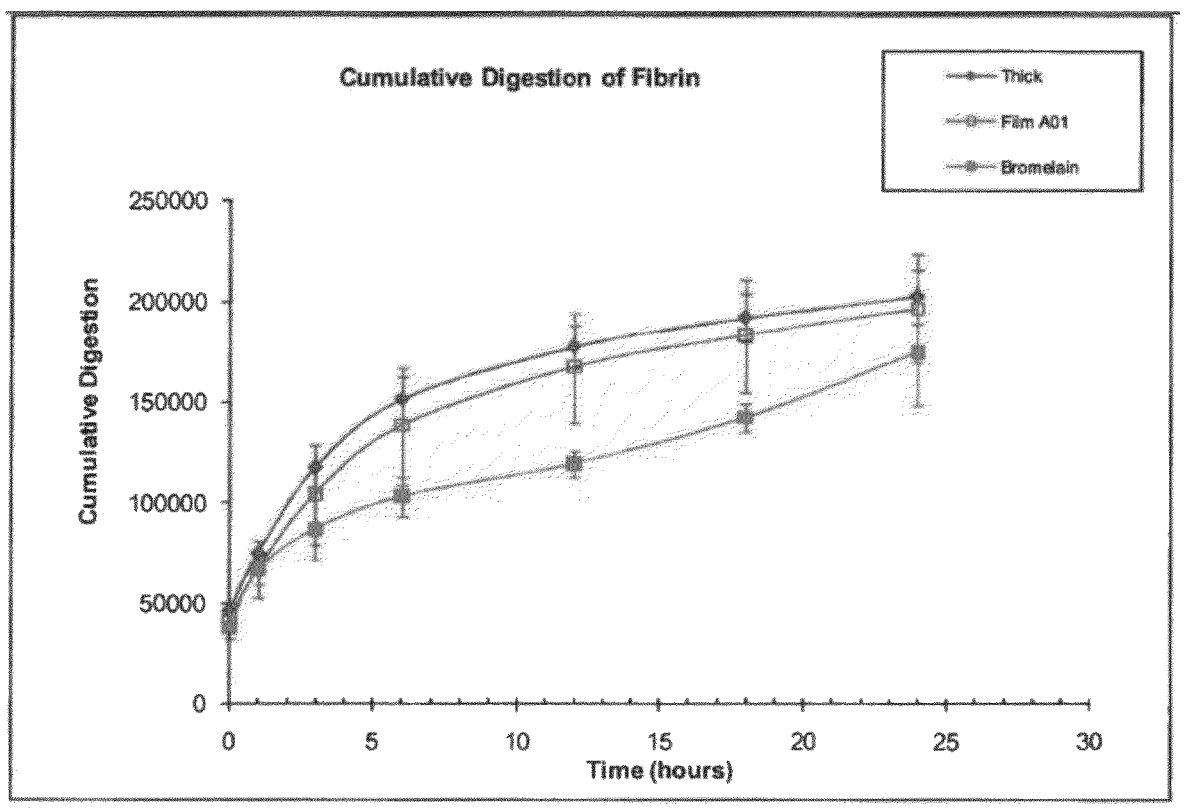
FIG. 4. A debridement experiment conducted in vitro using artificial eschar prepared using fibrin. Film containing thermolysin was compared with a thermolysin gel and a Bromelain gel. Both the film and the thermolysin gel digested fibrin more effectively than the Bromelain gel, which contained 10% bromelain.
Figure 6:
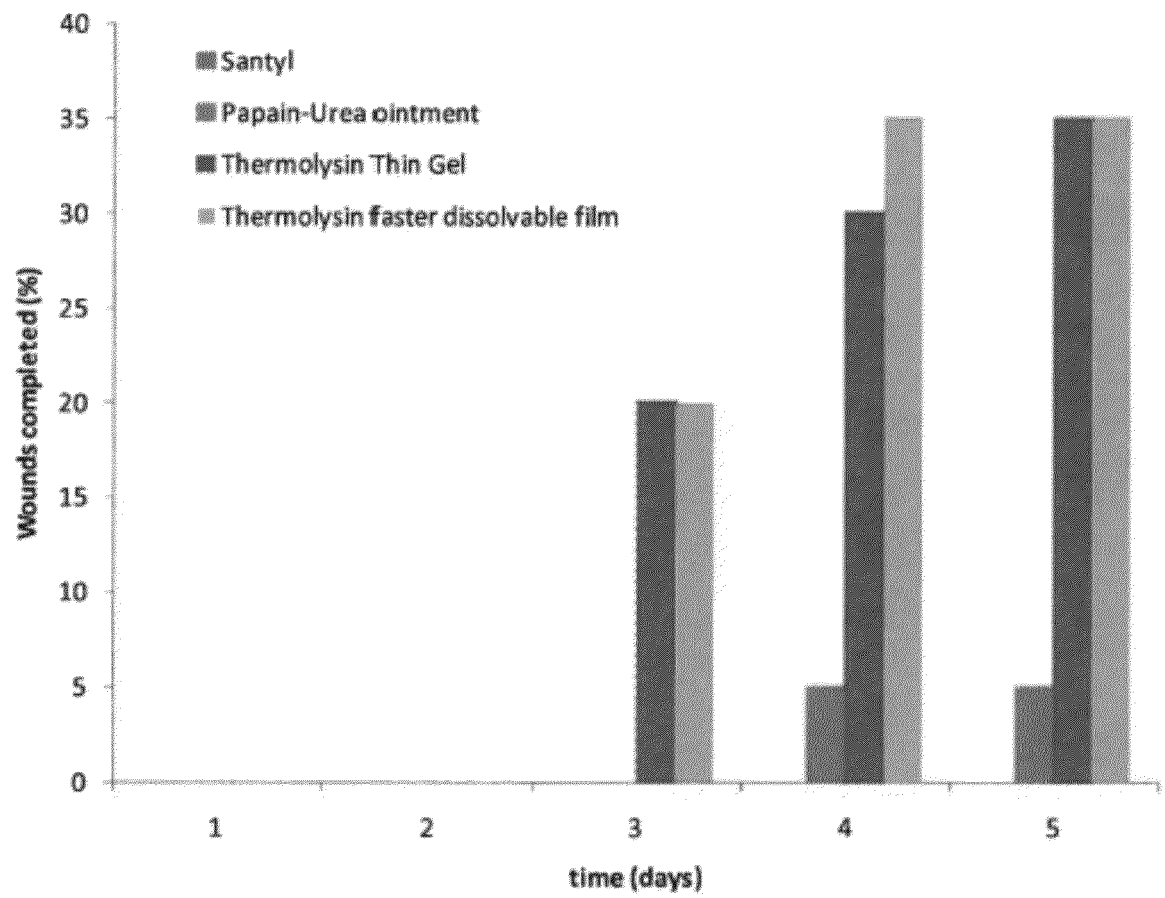
FIG. 6. In vivo pig study on the debridement efficacy of a thermolysin film and gel, a papain-urea ointment and SANTYL® collagenase ointment.

| Lot | Description | HEC (wt %) | HPMC HMW (wt %) | HPMC LMW (wt %) | HPC SL (wt %) | PEG-600 (wt %) | Sorbitol (wt %) | Gel Formation (h) | Viscosity (cps) |
|---|---|---|---|---|---|---|---|---|---|
| (45 g) 038-0406802 | Prototype | 10 | 0 | 50 | 0 | 21 | 10 | <1 h | 11300 |
| (45 g) 038-0301801 | Prototype | 33 | 30 | 0 | 0 | 23 | 0 | >1 h | 39400 |
| (45 g) 038-0302801 | Prototype | 35 | 31 | 0 | 0 | 23 | 0 | >1 h | 38200 |
| (45 g) 038-0330801 | Prototype (closes to "fast dissolving film" in FIG. 6 and "thick film" in FIGS. 3-4 | 30 | 0 | 30 | 0 | 20 | 10 | >1 h | 22600 |
| 038-0330803 | Prototype | 40 | 0 | 20 | 0 | 20 | 10 | >1 h | 8000 |
|  | Prototype | 50 | 0 | 10 | 0 | 20 | 10 | >1 h | 1200 |

Figure 2:
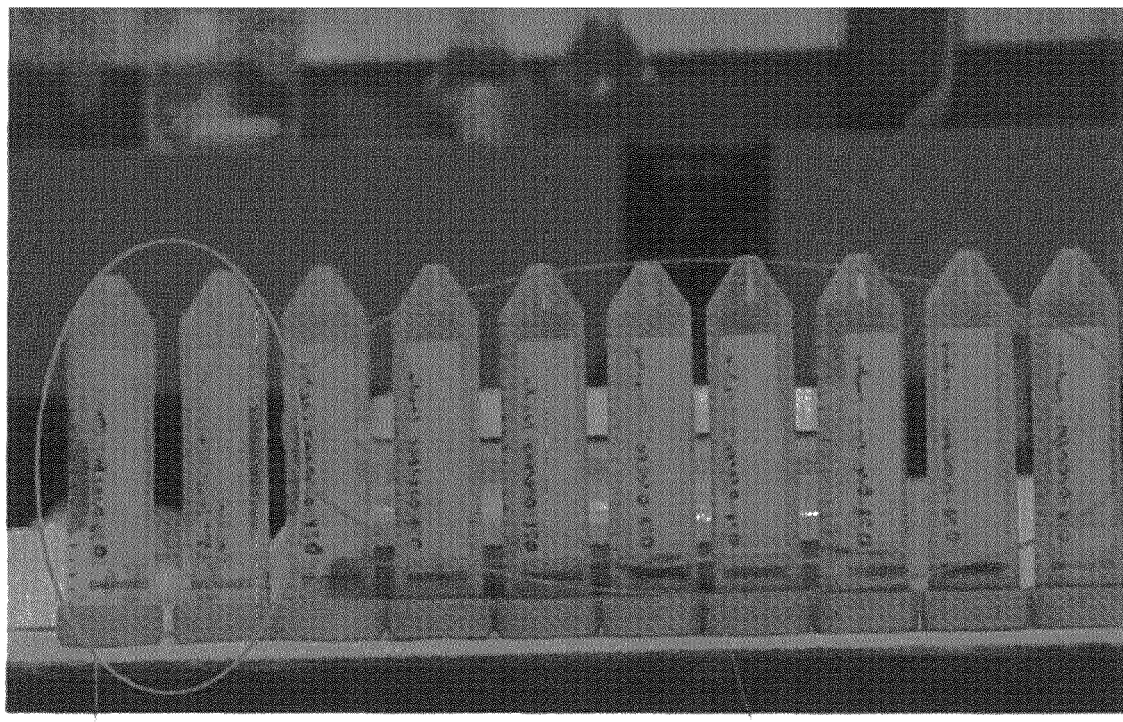
FIG. 2. A photograph illustrating the physical appearance of the gel formed from dissolved films. The dissolved films are pictured inside laboratory tubes that have been inverted. The films that dissolve into a more viscous gel are more likely to stay in the wound bed.

The dissolving characteristics can be visualized by inverting gels in laboratory tubes, as pictured in FIG. 2. The ideal film provides a hydrogel that is viscous enough to stay in the wound bed such that it will not "leak off" the wound.

2. Use of Dissolvable, Gel-Forming Films for In Vitro Wound Debridement

A debridement experiment was conducted in vitro using artificial eschar prepared using collagen, elastin, and fibrin. A dissolvable, gel-forming film containing thermolysin (called "Film A01," see Table 2) was compared with a thermolysin thick film (see Table 3) and a Bromelain gel (see Table 4).

TABLE 2

Formulation of "Film A01" containing thermolysin*

| Part # | Ingredient | Actual % |
|---|---|---|
| DOW | Methocel K 15M (Hydroxypropylmethylcellulose) | 32.14807702 |
| Aquaion | Hydroxy ethylcellulose (HEC) | 34.89760366 |
| Amano | Thermolysin | 5.0794876 |
| Sensient | FDC Blue#1 | 0.013333655 |
| Sigma-Aldrich | NaCl | 2.984198965 |
| Sigma-Aldrich | CaCl2 | 1.537052948 |
| DOW | PEG-600 | 23.34024552 |
|  |  | 99.9999994 |

*DI water was used to mix the ingredients of the film prior to dehydration.

TABLE 3

Formulation of "Thick Film" containing thermolysin^

| Part # | Ingredient | Actual % |
|---|---|---|
| DOW | Methocel K 15M (Hydroxypropylmethylcellulose) | 30.51795977 |
| Aquaion | Hydroxy ethylcellulose (HEC) | 33.43989209 |
| Sigma-Aldrich | Thermolysin | 5.011405287 |
| Spectrum | Urea | 2.017881464 |
| BASF | Poloxamer-407 | 1.000949122 |
| Sensient | FDC Blue#1 | 0.012969717 |
| Sigma-Aldrich | NaCl | 3.01017301 |
| Sigma-Aldrich | CaCl2 | 1.513411098 |

TABLE 3-continued

Formulation of "Thick Film" containing thermolysin^

| Part # | Ingredient | Actual % |
|---|---|---|
| DOW | PEG-600 | 23.47535367 |
|  |  | 99.9999952 |

^Tris Buffer (10 mM, pH = 7.5) was used to mix the ingredients of the film prior to dehydration.

TABLE 4

Formulation of Bromelain Gel

| Part # | Ingredient | Actual % |
|---|---|---|
| Lubrizol | Carbomer 934K | 1.637989696 |
| EMD | Na2HPO4 | 2.775347526 |
| Sigma | NaOH | 1.219986391 |
| Spectrum | Bromelain | 9.988334791 |
| NA | Water | 84.37834159 |
|  |  | 100 |

The films were prepared by mixing the ingredients (absent enzyme and salts) until homogenous. Next, the enzyme was added as a solution or dispersion in buffer with the stated amounts of salts (e.g., NaCl and CaCl$_2$). The final mixture, which included all ingredients, was stirred until homogeneous. The mixture (a viscous gel) was then centrifuged to remove air bubbles and applied into petri dishes. The dishes were left to dry on even surfaces with appropriate ventilation under normal lab conditions. After about 48 hours of drying, the films were cut into custom size pieces for use.

The dissolvable, gel-forming film digested collagen equally as well as the thermolysin thick film (labeled "Thick" in FIGS. 3 and 4). Both outperformed Bromelain gel, which contained 10% bromelain (see FIGS. 3 and 4).

3. Use of Dissolvable, Gel-Forming Films for In Vivo Wound Debridement

Figure 5:
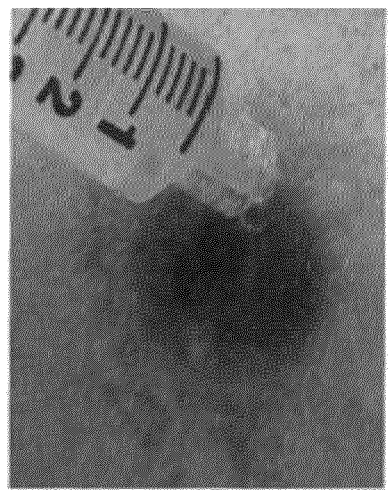
FIG. 5. An illustration of one procedure for applying the film to a wound. First, the wound is moistened with saline. Second, the film is applied to the moistened wound. After the film is applied to the wound, it is moistened with saline. A nonstick wound dressing, presoaked with saline, is then applied on top of the film. The dressing is then secured with, for example, medical dressing and tape.
Figure 5:
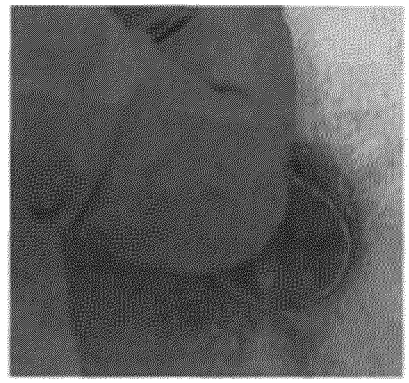
Figure 5:
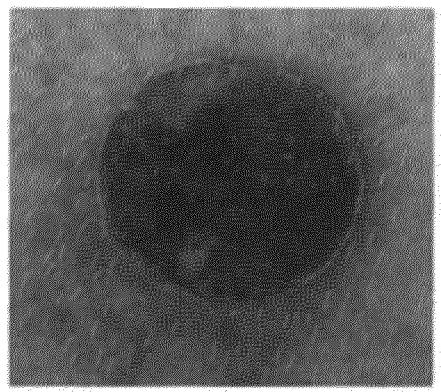
Figure 5:
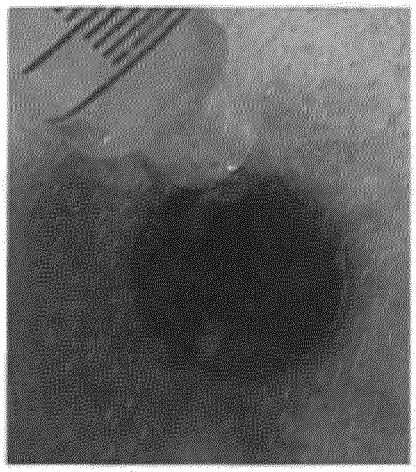
Figure 5:
Figure 5:
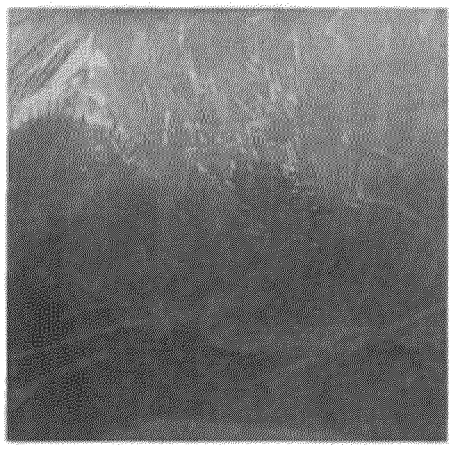

An in vivo pig burn model was used to test films of the present invention. Burn wounds were generated on the backs of pigs by burning the skin with a hot metal rod. Wounds were allowed to form eschars prior to starting treatment. All wounds were treated once a day with either a thermolysin film (Table 5), a thermolysin thin gel (Table 6), a papain-urea ointment (Table 7), or SANTYL® Collagenase (a sterile enzymatic debriding ointment that contains 250 collagenase units per gram of white petrolatum USP), available from Healthpoint® Biotherapeutics). FIG. 5 illustrates how the film was applied to the wounds in this model.

TABLE 5

Formulation of the faster dissolving thin film containing thermolysin[#]

| Part # | Ingredient | Actual % |
|---|---|---|
| DOW | Methocel K 15M (Hydroxypropylmethylcellulose) | 29.68061473 |
| Aquaion | Hydroxy ethylcellulose (HEC) | 32.32091482 |
| Amano | Thermolysin | 11.81943989 |
| Sigma-Aldrich | CaCl2 | 1.503150151 |
| Sigma-Aldrich | NaCl | 3.00721075 |
| DOW | PEG-600 | 21.66866965 |
|  |  | 100 |

[#]Tris Buffer (10 mM, pH = 7.5) was used to mix the ingredients of the film prior to dehydration.

TABLE 6

Formulation of the thermolysin thin gel

| Part # | Ingredient | Actual % |
|---|---|---|
| Aquaion | Hydroxy ethylcellulose (HEC) | 2.992194889 |
| NA | Water (Tris Buffer, 1.19 mM pH = 7.5) | 80.57284539 |
| Amano | Thermolysin | 0.795189906 |
| Sigma-Aldrich | NaCl | 0.280212465 |
| Sigma-Aldrich | CaCl2 | 0.108678777 |
| Fluka | Methyl paraben | 0.249349574 |
| Fluka | Propyl Paraben | 0.049964009 |
| Sigma-Aldrich | Propylen Glycol | 14.95156503 |
|  |  | 100 |

TABLE 7

Formulation of the papain-urea cream

| Part # | Ingredient | Actual % |
|---|---|---|
| 713950 | Emulsifying Wax | 10.9589348 |
| NA | DI Water | 50.581992 |
| Spectrum | Isopropyl Palmitate, NF | 4.01397068 |
| Spectrum | Glycerin | 4.9677855 |
| Spectrum | Urea | 9.97531328 |
| Sigma | Beta-Lactose | 15.9167847 |
| DPT, 160278 | Papain, USP | 2.3067084 |
| Fisher | KH2PO4 | 0.99885607 |
| Fluka | Methyl paraben | 0.19970498 |
| 155530 | Propyl Paraben | 0.07994823 |
|  |  | 99.999999 |

The films were prepared as described above in Example 2. The faster dissolving film (Table 5) dissolved in water at a rate of 6 mg/min (as compared to 2.2 mg/min for Film A01 described in Table 2). The number of wounds that completed debridement was determined to compare the efficacy of the four different treatments. The percentage of wounds that were fully debrided for the different treatments after 1-5 days is illustrated in FIG. 6. The thermolysin thin gel and thermolysin faster dissolving film greatly out-performed either the papain-urea ointment or SANTYL® Collagenase in terms of their ability to debride wounds.

The invention claimed is:

1. A method of debriding a wound comprising topically applying a dissolvable, gel-forming film to a wound in need of debridement, wherein the dissolvable, gel-forming film comprises:
 (a) a water-soluble cellulose ether;
 (b) a hydrophilic rheological modifying agent; and
 (c) thermolysin,
 wherein the dissolvable, gel-forming film has a water content of less than 15% w/w, and
 wherein the dissolvable, gel-forming film is capable of forming a hydrogel when 1 gm of gel-forming film is contacted with 20 ml of water or other aqueous medium.

2. The method of claim 1, wherein the wound is a chronic wound.

3. The method of claim 2, wherein the chronic wound is a diabetic foot ulcer, a venous leg ulcer, an arterial leg ulcer, a decubitus ulcer, a stasis ulcer, a dermal ulcer, a burn, or a pressure ulcer.

4. The method of claim 1, wherein the wound includes necrotic tissue.

5. The method of claim 4, wherein the necrotic tissue is an eschar.

6. The method of claim 1, wherein an aqueous medium is applied to the wound before the dissolvable, gel-forming film is applied to the wound or wherein an aqueous medium is applied to the dissolvable, gel-forming film after said film is applied to the wound.

7. The method of claim 6, wherein the aqueous medium is a saline solution.

8. The method of claim 1, wherein a bandage, wound dressing, or gauze is applied onto the dissolvable, gel-forming film after said film is applied to the wound.

9. The method of claim 1, wherein the water-soluble cellulose ether is a hydroxyalkyl cellulose ether.

10. The method of claim 9, wherein the hydroxyalkyl cellulose ether is hydroxyethylcellulose, hydroxypropylcellulose, or hydroxypropylmethylcellulose, or any combination thereof.

11. The method of claim 10, wherein the hydroxyalkyl cellulose ether comprises 25 to 35% w/w of hydroxyethylcellulose and 25 to 35% w/w of hydroxypropylmethylcellulose.

12. The method of claim 1, wherein the dissolvable, gel-forming film comprises 50 to 70% w/w or 55 to 65% w/w of the water-soluble cellulose ether.

13. The method of claim 1, wherein the hydrophilic rheological modifying agent is a polyol.

14. The method of claim 13, wherein the polyol is polyethylene glycol.

15. The method of claim 1, wherein the dissolvable, gel-forming film comprises 15 to 25% w/w of the hydrophilic rheological modifying agent.

16. The method of claim 1, wherein the dissolvable, gel-forming film comprises 5 to 15% w/w of the thermolysin.

17. The method of claim 1, wherein the dissolvable, gel-forming film further comprises a metal salt.

18. The method of claim 17, wherein the metal salt is sodium chloride or calcium chloride or a mixture thereof.

19. The method of claim 1, wherein the dissolvable, gel-forming film further comprises a preservative.

20. The method of claim 19, wherein the preservative is methylparaben, propylparaben, or phenoxyethanol, or a mixture thereof.

21. The method of claim 1, wherein the hydrogel that is formed has a viscosity of 1,000 to 100,000 cps, as measured using a Brookfield RV Model Viscometer using small sample adapter with spindle #SC4-14 and chamber #SC4-6R, at 10 rpm at room temperature, reading taken at 1 minute.

* * * * *